United States Patent [19]
Townsend et al.

[11] Patent Number: 5,851,523
[45] Date of Patent: *Dec. 22, 1998

[54] ISOLATED, PEPTIDES DERIVED FROM MAGE TUMOR REJECTION ANTIGEN PRECURSORS WHICH COMPLEX WITH HLA-A2 MOLECULES AND USES THEREOF

[75] Inventors: Alan Townsend; Judy Bastin, both of Oxford, England; Thierry Boon-Falleur, Brussels, Belgium; Pierre van der Bruggen, Brussels, Belgium; Pierre Coulie, Brussels, Belgium; Thomas Gajewski, Brussels, Belgium

[73] Assignee: Ludwig Institute for Cancer Research., London, England

[*] Notice: The term of this patent shall not extend beyond the expiration date of Pat. No. 5,585,461.

[21] Appl. No.: 290,381

[22] Filed: Aug. 15, 1994

Related U.S. Application Data

[63] Continuation-in-part of Ser. No. 261,160, Jun. 17, 1994, Pat. No. 5,591,430, which is a continuation-in-part of Ser. No. 217,186, Mar. 24, 1994, Pat. No. 5,585,461.

[51] Int. Cl.$^6$ .......................... A61K 39/00; A61K 39/385
[52] U.S. Cl. ..................... 424/185.1; 427/193.1; 427/277.1; 530/300; 530/328; 422/61; 206/570
[58] Field of Search ...................... 530/300, 328, 530/402, 351; 424/185.1, 85.2, 184.1, 193.11, 193.1, 277.1; 422/61; 206/570

[56] References Cited

U.S. PATENT DOCUMENTS 5,342,774  8/1994  Boon et al. ................... 435/240.2

FOREIGN PATENT DOCUMENTS

WO9403205  2/1994  WIPO .

OTHER PUBLICATIONS

W. F. Paul (ed.), Fundamental Immunology, 3rd edition, pp. 116–117, 517–518, 739–740, 775, and 1402. Raven Press, New York, 1993.

Townsend et al., The Epitopes of Influenza Nucleoprotein Recognized–by Cytotoxic T Lymphocytes Can Be Defined With Short Synthetic Peptides, Cell 44: 959–968 (Mar. 28, 1986).

Bjorkman et al., "The foreign antigen binding site and T cell–recognition regions of class I histocompatibility antigens", Nature 329: 512–518 (Oct. 8, 1987).

Van der Bruggen et al., "A Gene Encoding an Antigenic Recognized–by Cytolytic T Lymphocytes on a Human Melanoma", Science 254: 1643–1647 (1991).

Traversari et al., "A Nonapeptide Encoded by Human Gene MAGE–1–Is Recognized on HLA–A1 by Cytolytic T Lymphocytes Directed Against Tumor Antigen MZ2–E", J. Exp. Med 176: 1453–1457 (Nov. 1992).

Celis et al., "Induction of anti–tumor cytotoxic T lymphocytes–in normal humans using primary cultures and synthetic peptide epitopes", Proc. Natl. Acad. Sci. USA 91: 2105–2109 (Mar. 1994).

Coulie et al., "A New Gene Coding for a Differentiation Antigen–Recognized by Autologous Cytolytic T Lymphocytes on HLA–A2 Melanomas", J. Exp. Med. 180: 35–42 (Jul., 1994) (Not Prior Art).

Engelhard et al., "Structure of Peptides Associated with Class–I and Class II MHC Molecules", Ann. Rev. Immunol. 12: 181–207 (1994).

Ruppert et al., "Prominent Role of Secondary Anchnor Residues in–Peptide Binding to HLA–A2.1 Molecules", Cell 74: 929–937 (Sep. 10, 1993).

*Primary Examiner*—Thomas M. Cunningham
*Attorney, Agent, or Firm*—Fulbright & Jaworski, LLP

[57] ABSTRACT

Tumor rejection antigens derived from MAGE tumor rejection precursors have been identified. These "TRAS" bind to the MHC-class I molecule HLA-A2, and the resulting complexes stimulate the production of cytolytic T cell clones which lyse the presenting cells. The peptides and complexes may be used diagnostically, therapeutically, and as immunogens for the production of antibodies, or as targets for the generation of cytolytic T cell clones.

7 Claims, 12 Drawing Sheets

SEQUENCE LISTING ( 1 ) GENERAL INFORMATION:

( i i i ) NUMBER OF SEQUENCES: 13

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

```
Gly  Leu  Glu  Ala  Arg  Gly  Glu  Ala  Leu
 1                    5
```

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Ala  Leu  Ser  Arg  Lys  Val  Ala  Glu  Leu
 1                    5
```

( 2 ) INFORMATION FOR SEQ ID NO: 3:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

```
Cys  Leu  Gly  Leu  Ser  Tyr  Asp  Gly  Leu
 1                    5
```

( 2 ) INFORMATION FOR SEQ ID NO: 4:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Ile  Leu  Gly  Asp  Pro  Lys  Lys  Leu  Leu
 1                    5
```

( 2 ) INFORMATION FOR SEQ ID NO: 5:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

His Leu Tyr Ile Phe Ala Thr Cys Leu
 1              5

( 2 ) INFORMATION FOR SEQ ID NO: 6:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

Phe Leu Trp Gly Pro Arg Ala Leu Val
 1              5

( 2 ) INFORMATION FOR SEQ ID NO: 7:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

Thr Leu Val Glu Val Thr Leu Gly Glu Val
 1              5                    1 0

( 2 ) INFORMATION FOR SEQ ID NO: 8:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

Ala Leu Ser Arg Lys Val Ala Glu Leu Val
 1              5                    1 0

( 2 ) INFORMATION FOR SEQ ID NO: 9:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

Leu Leu Lys Tyr Arg Ala Arg Glu Pro Val
 1              5                    1 0

( 2 ) INFORMATION FOR SEQ ID NO: 10:

( i ) SEQUENCE CHARACTERISTICS:
        ( A ) LENGTH: 10 amino acids

-continued (B) TYPE: amino acid
(D) TOPOLOGY: linear (ii) MOLECULE TYPE: protein (xi) SEQUENCE DESCRIPTION: SEQ ID NO: 10:

Ala Leu Val Glu Thr Ser Tyr Val Lys Val
1               5                   10

(2) INFORMATION FOR SEQ ID NO: 11:

(i) SEQUENCE CHARACTERISTICS:
    (A) LENGTH: 9 amino acids
    (B) TYPE: amino acid
    (D) TOPOLOGY: linear (ii) MOLECULE TYPE: protein (xi) SEQUENCE DESCRIPTION: SEQ ID NO: 11:

Gly Ile Leu Gly Phe Val Phe Thr Leu
1               5

(2) INFORMATION FOR SEQ ID NO: 12:

(i) SEQUENCE CHARACTERISTICS:
    (A) LENGTH: 6 amino acids
    (B) TYPE: amino acid
    (D) TOPOLOGY: linear (ii) MOLECULE TYPE: protein (ix) FEATURE: The second Xaa in the sequence may be any 4 or
     5 amino acids (xi) SEQUENCE DESCRIPTION: SEQ ID NO: 12:

Xaa Leu Xaa Gly Xaa Leu
1               5

(2) INFORMATION FOR SEQ ID NO: 13:

(i) SEQUENCE CHARACTERISTICS:
    (A) LENGTH: 6 amino acids
    (B) TYPE: amino acid
    (D) TOPOLOGY: linear (ii) MOLECULE TYPE: protein
    (IX) FEATURE: The second Xaa in the sequence may be any 4 or
         5 amino acids (xi) SEQUENCE DESCRIPTION: SEQ ID NO:13:

Xaa Leu Xaa Gly Xaa Val
1               5

ISOLATED, PEPTIDES DERIVED FROM MAGE TUMOR REJECTION ANTIGEN PRECURSORS WHICH COMPLEX WITH HLA-A2 MOLECULES AND USES THEREOF

RELATED APPLICATIONS

This application is a continuation-in-part of Ser. No. 08/261,160 filed June 17, 1994 now U.S. Pat. No. 5,591,450 which is a continuation-in-part of Ser. No. 07/217,186 filed Mar. 24, 1994 now U.S. Pat. No. 5,585,467. The present case claims priority of both applications.

FIELD OF THE INVENTION

This invention relates to immunogenetics and to peptide chemistry. More particularly, it relates to peptides, especially deca- and nonapeptides useful in various ways, including immunogens and as ligands for HLA-A2 molecules. More particularly, it relates to a so-called "tumor rejection antigen", derived from tumor rejection antigen precursors, and presented by the MHC-class I molecule HLA-A2.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum$^-$ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum$^-$ antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum$^-$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum$^-$ variants fail to form progressive tumors because they initiate an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum$^-$ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum$^-$ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 126: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum$^-$" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum$^-$ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

PCT application PCT/US92/04354, filed on May 22, 1992 assigned to the same assignee as the subject application, teaches a family of human tumor rejection antigen precursor coding genes, referred to as the MAGE family. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Barinaga, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide. As described herein, while this "rule" is generally true, there is some leeway as to the length of peptides which MHC-class I molecules will bind.

Studies on the MAGE family of genes have now revealed that a particular nonapeptide is in fact presented on the surface of some tumor cells, and that the presentation of the requires that the presenting molecule be HLA-A1. Complexes of the MAGE-1 tumor rejection antigen (the "TRA" or "nonapeptide") leads to lysis of the cell presenting it by cytolytic T cells ("CTLs").

Attention is drawn, e.g., to concurrently filed application Ser. No. 08/217,188, filed Mar. 24, 1994 to Traversari et al., and Ser. No. 08/217,187 filed Mar. 24, 1994 to Melief et al., both of which present work on other, MAGE-derived peptides.

Research presented in, e.g., U.S. patent application Ser. No. 07/938,334 filed Aug. 31, 1992, and in U.S. patent application Ser. No. 08/073,103, filed Jun. 7, 1993, when comparing homologous regions of various MAGE genes to the region of the MAGE-1 gene coding for the relevant nonapeptide, there is a great deal of homology. Indeed, these observations lead to one of the aspects of the invention disclosed and claimed therein, which is a family of nonapeptides all of which have the same N-terminal and C-terminal amino acids. These nonapeptides were described as being useful for various purposes which includes their use as immunogens, either alone or coupled to carrier peptides. Nonapeptides are of sufficient size to constitute an antigenic epitope, and the antibodies generated thereto were described as being useful for identifying the nonapeptide, either as it exists alone, or as part of a larger polypeptide.

These references, especially Ser. No. 08/073,103, showed a connection between HLA-A1 and MAGE-3; however, only about 26% of the Caucasian population and 17% of the negroid population presents HLA-A1 molecules on cell surfaces. Thus, it would be useful to have additional information on peptides presented by other types of MHC molecules, so that appropriate portions of the population may benefit from the research discussed supra.

It has now been found that antigen presentation of MAGE-3 derived peptides is not limited to HLA-A1 molecules. The invention set forth, in the disclosure which follows, identifies peptides from MAGE-3 and other MAGE TRAPS, which complex with MHC class I molecule HLA-A2. The ramifications of this discovery, which include therapeutic and diagnostic uses, are among the subjects of the invention, set forth in the disclosure which follows.

BRIEF DESCRIPTION OF THE FIGURES

FIG. 6A involves tests with CTL clone 279/19, and FIG. 6B used CTL clone 297/22.

In FIG. 7A, CTL 279/19 is used, while CTL 297/22 is used to generate the data of FIG. 7B.

DETAILED DESCRIPTION OF PREFERRED EMBODIMENTS

Example 1

Figure 1:
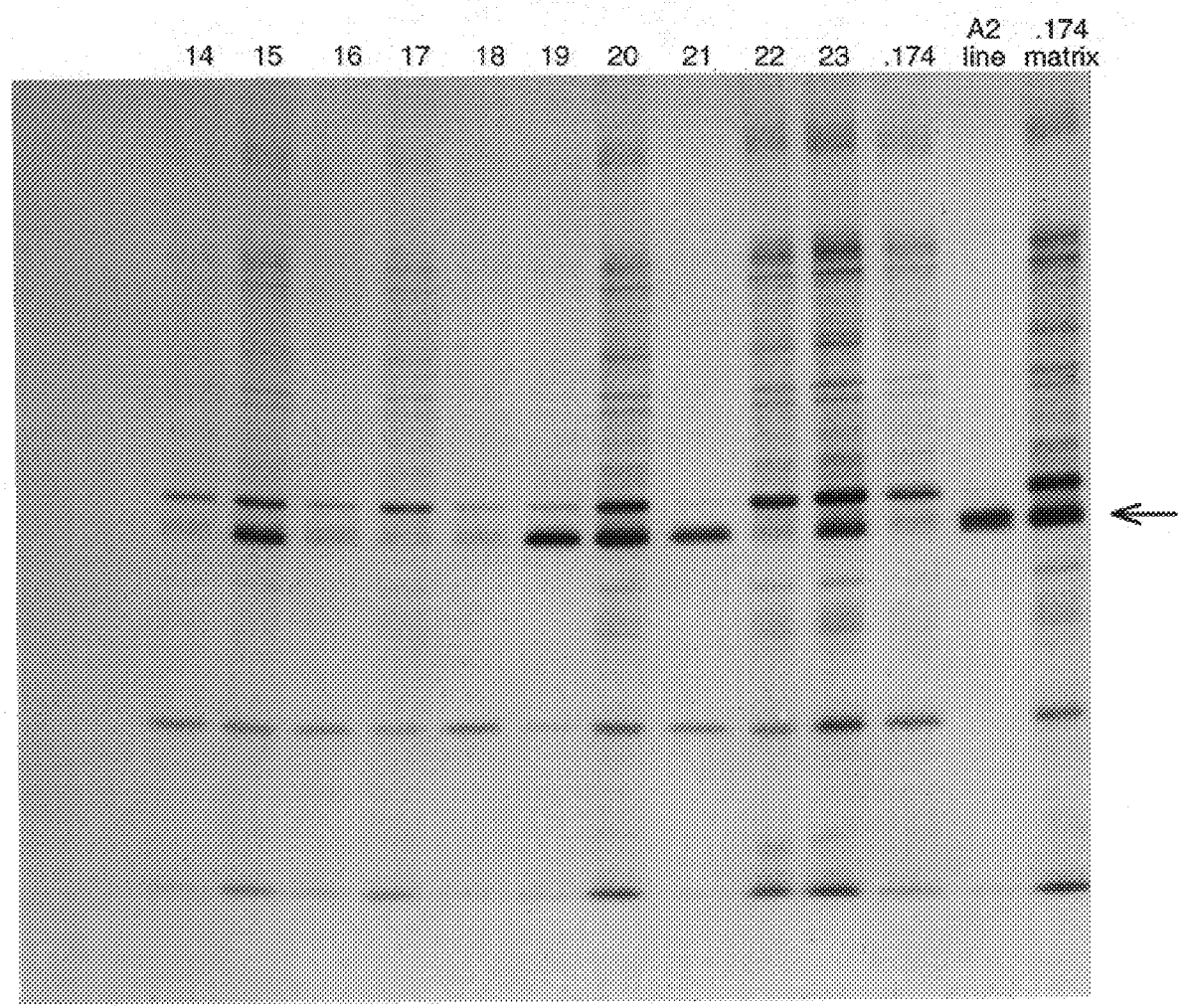
FIG. 1 presents the results of initial screening data on the peptides described herein.

The methodologies employed in this set of experiments are akin to those described by Elvin et al., J. Imm. Meth. 158: 161–171 (1993), Townsend et al., Nature 340: 443–448 (Aug. 10, 1989), and Townsend et al., Cell 62: 285–290 (Jul. 27, 1990), all of which are incorporated by reference in their entirety.

Cell line 0.174 as described was used. It is an HLA-A2 presenting cell line deficient in the pathway which supplies peptides to the endoplasmic reticulum, the site of assembly of MHC class-I heterodimers. The cell line can assemble MHC class-I molecules, but these are unstable and, on cell lysis, dissociate into free heavy and light chains during overnight incubation. The heterodimers can, however, be stabilized in vitro via addition of appropriate peptide ligands. (Townsend et al., Nature 340: 443–448 (1989); Townsend et al., Cell 62: 285–295 (1990)). Thus, the stabilized molecules can be immunoprecipitated with antibodies specific for the MHC class-I molecule.

In the first part of these experiments, peptides were tested to determine if they facilitated assembly of HLA-A2 in the cell line. The peptides tested included the following:

| | | | | | | | | | | |
|---|---|---|---|---|---|---|---|---|---|---|
| SEQ ID NO: 1 | Gly | Leu | Glu | Ala | Arg | Gly | Glu | Ala | Leu | |
| SEQ ID NO: 2 | Ala | Leu | Ser | Arg | Lys | Val | Ala | Glu | Leu | |
| SEQ ID NO: 3 | Cys | Leu | Gly | Leu | Ser | Tyr | Asp | Gly | Leu | |
| SEQ ID NO: 4 | Ile | Leu | Gly | Asp | Pro | Lys | Lys | Leu | Leu | |
| SEQ ID NO: 5 | His | Leu | Try | Ile | Phe | Ala | Thr | Cys | Leu | |
| SEQ ID NO: 6 | Phe | Leu | Trp | Gly | Pro | Arg | Ala | Leu | Val | |
| SEQ ID NO: 7 | Thr | Leu | Val | Glu | Val | Thr | Leu | Gly | Glu | Val |
| SEQ ID NO: 8 | Ala | Leu | Ser | Arg | Lys | Val | Ala | Glu | Leu | Val |
| SEQ ID NO: 9 | Leu | Leu | Lys | Tyr | Arg | Ala | Arg | Glu | Pro | Val |
| SEQ ID NO: 10 | Ala | Leu | Val | Glu | Thr | Ser | Tyr | Val | Lys | Val |

Cells were labelled by exposure to [$^{35}$S] methionine (aliquots of 1–2×10$^7$ cells, labeled with 100–200 μCi, 60 minutes of contact). The cells were then washed, once, with phosphate buffered saline, and then resuspended in 10 ml of lysis buffer (0.5% NP-40; 0.5% Mega 9, 150 mM NaCl, 5 mM EDTA, 50 mM Tris [pH 7.5], 2 mM phenylmethylsulfonylflouride, 5 mM iodoacetamide). The lysates were then incubated with peptide (10 μM and 20 μM), for 15–18 hours. Nuclei were then pelleted in a microfuge, and the lysates were precleared, overnight, at 4° C. with 0.2 ml of washed, 10% (w/v) Staphylococcus A organisms. Lysates were divided into two portions, and monoclonal antibody BB7.2 was added to a final concentration of 5 ug/ml. This mAb is a conformation specific, HLA-A2 recognizing mAb described by Parham et al., Hum. Immunol. 3: 277–299 (1981). The mixtures were incubated for 90 minutes on ice, followed by addition of bovine serum albumin to 1% (w/v), and 100 ul of 5% (w/v) protein-A Sepharose beads. Tubes were rotated for 45 minutes, after which beads were washed, four times, with 1 ml wash buffer (0.5% NP-40, 150 mM NaCl, 5 mM EDTA, 50 mM Tris [pH 7.5]). Samples were eluted, and analyzed on 12% polyacrylamide gels, in accordance with Townsend et al., Nature 340: 443–448 (1989).

FIG. 1 shows results from these experiments for the peptides which gave positive results. These were SEQ ID NOS: 2, 6, 7, 8 and 10, as is evidenced by the dark band, indicated by HC (heavy chain) common to all of the gels, and represents immunoprecipitated MHC molecule (HLA-A2) that had complexed with the peptide prior to electrophoresis.

The figure shows work with SEQ ID NOS: 2, 6, 7, 8 and 10, running from left to right. The vertical bar separates SEQ ID NO: 5 from gels marked "0.174", "A2 line", and "0.174 matrix". 0.174 is a "negative" control for the heavy chain of the MHC class I molecule. As noted supra, this cell line does not present stable MHC-class I molecules without exogenous peptide, and as mAb BB7.2 is conformation specific, it should not precipitate uncomplexed MHC-class I molecules. "A2" refers to a known cell line presenting HLA-A2 (the line is LBL 721, described by DeMars et al., Hum. Immunol. 11: 77 (1984)), but any cell presenting stable HLA-A2 molecules would function in the same way. "0.174 matrix" shows results when 0.174 cell line was incubated together with the control peptide GILGFVFTL (SEQ ID NO: 11), which is derived from influenza virus and is known to be presented by HLA-A2.

The results show the stabilization of the MHC-class I molecule, by the fact that the bands for "HC" (heavy chain) are comparable to those obtained for A2 and 0.174 matrix. In fact, the MHC molecule is disrupted by the reducing gel; however, the heavy chain molecules will be bound by the comformation specific mAb if stabilized prior to reduction.

This is in fact what the gels show—i.e.—that the recited peptides bound to the HLA-A2 molecules, and stabilized them.

Example 2

Once binding peptides were identified, a series of titration experiments were carried out. In these, varying concentrations of peptides, in accordance with Townsend et al., Cell 62: 285–295 (Jul. 27, 1990) at 293, incorporated by reference herein, were added to lysates of the cell line referred to supra, and immunoprecipitated to determine the concentration which was the best concentration for the binding of the peptide.

Figure 2:
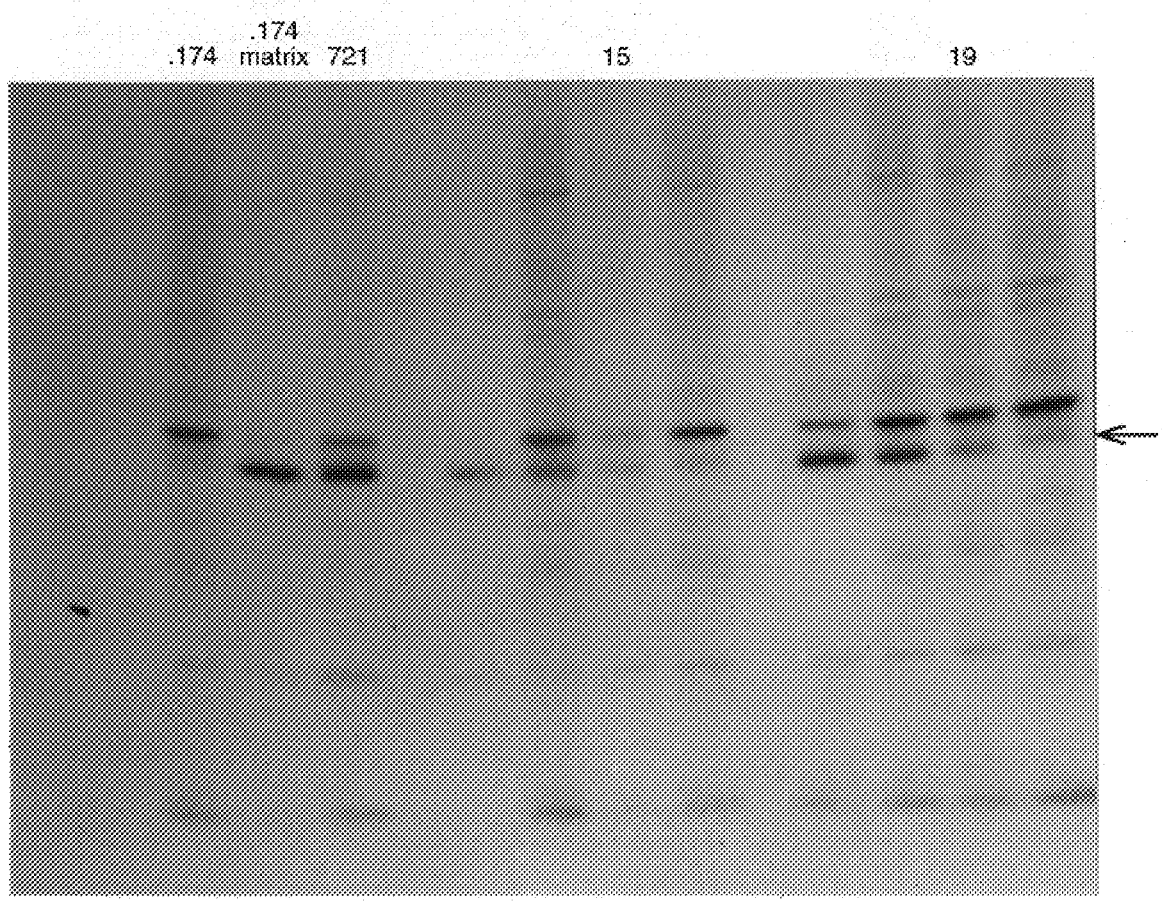
FIG. 2 shows titration data obtained using SEQ ID NO: 2 and SEQ ID NO: 6.

FIG. 2 shows the results obtained for two of the peptides i.e., SEQ ID NO: 2 and 6. The peptides were titrated against a known HLA-A2 binding peptide SEQ ID NO: 11, with 10 fold dilutions starting at 20 μM, and decreasing to 2, 0.2 and 0.002 μM.

Experiments were carried out with these peptides (i.e., SEQ ID NOS: 2 and 6). In the case of SEQ ID NO: 2, in experiments not reported here the peptide titrated at 5–10 nM. This was comparable to the control (SEQ ID NO: 11).

Example 3

A series of experiments were carried out to show the ability of the peptide SEQ ID NO: 6 to provoke lysis by cytolytic T lymphocytes ("CTLs") specific to complexes of the peptide and HLA-A2. The first steps in these experiments are described herein.

Peripheral blood lymphocytes ("PBLs") were taken from a normal donor, i.e., one without any cancer tumors. The donor, referred to as "LB705", was typed as HLA-A1, A2, B8, B27. At the start ("day 0"), PBLs from the donor were suspended, at 10$^6$ cells/ml, in Iscove's medium and 10% fetal calf serum and "AAG" (asparagine+arginine+glutamine), and 20 ug/ml of rabbit antihuman IgM antibody, and 20 ng/ml recombinant human IL-4 ("r-hu-IL4"), and 0.005% Pansorbin cells. The mixture was distributed into 24-well tissue culture plates (2 ml per well).

At day 3, the cells were centrifuged and resuspended in Iscove's medium and 10% human serum and AAG and 20 ng/ml r-hu-IL-4.

Two days later, on day 5, the cells were again centrifuged, and resuspended in fresh Iscove's medium and 10% human serum and AAG and 20 ng/ml r-hu-IL-4, and 20 U/ml recombinant human γ-interferon.

On day 6, the cells were again centrifuged, and resuspended at $5 \times 10^6$ cells/ml in Iscove's medium without serum, and 50 ug/ml of the peptide of SEQ ID NO: 6, plus 2.5 ug/ml of human β2 microglobulin. The cells were incubated in this mixture for four hours at 37° C., and were then irradiated at 50 Gy. The cells were then centrifuged again, and resuspended in Iscove's medium and 10% human serum+AAG. The cells were then placed in individual wells of 24 well tissue culture plates, at 1 million cells per well.

Responder cells were then added. These were CD8+ T cells also obtained from donor LB705. Fractions of CD8+ cells had been secured from the donors' PBLs using well known techniques for separating T cell fractions. The responder cells were added to the wells, at $5 \times 10^6$ cells/well. Final volume was 2 ml. Following the addition of the cells, 1000 U/ml of recombinant human IL-6 ("r-hu-IL-6"), and 10 ng/ml of recombinant human IL-12 ("r-hu-IL-12") were added.

Seven days later, i.e., on day 13, the responder cells, i.e., the CD8+ cells, were restimulated. This was accomplished by transferring the mixed culture discussed above to autologous adherent cells, together with 10 U/ml r-hu-IL-2, and 5 ng/ml of r-hu-IL-7. The autologous adherent cells had been prepared previously, by incubating $5 \times 10^6$ irradiated (50 Gy) PBLs from LB705, in 1 ml Iscove's medium+10% human serum+AAG, at 37° C. for two hours. Any non-adherent cells were removed and 50 ug/ml of the peptide of SEQ ID NO: 6 and 2.5 ug/ml of human β2 microglobulin were added, in 0.5 ml of serum free medium. This mixture was incubated for two hours at 37° C., and then washed. The responder CD8+ cells were then added to them.

At day 21, another stimulation of the responder cells took place, by adding $2 \times 10^6$ PBLs, irradiated at 50 Gy, which had been incubated in serum free medium+50 ug/ml human β2 microglobulin plus 50 ug/ml of SEQ ID NO: 6 for two hours, followed by washing.

This protocol resulted in the generation of CTLs specific for complexes of SEQ ID NO: 6 and HLA-A2, which is shown in the following example.

Example 4

Experiments were carried out on day 28 to determine if peptides in accordance with the invention, when complexed to HLA-A2 molecules, would provoke lysis by CTLs.

Cells of line T2 were used. This cell line presents HLA-A2 molecules on its surface, but has an antigen processing defect which results in increased capacity for presenting exogenous peptides. See Cerundolo, et al, Nature 345: 449 (1990), which describes this cell line. Other equivalent cell lines are also available.

Samples of T2 cells were labelled with radioactive chromium ($^{51}$Cr), and incubated together with 1 μm of the peptide of SEQ ID NO: 6. The preincubation took place for one hour prior to introduction of CTLs. Control samples of T2 cells were not incubated with peptide.

CTLs were prepared by stimulating CD8+ cells with autologous APCs, preincubated with the peptide of SEQ ID NO: 6 for a period of 21 days, in accordance with example 3, supra.

Figure 3:
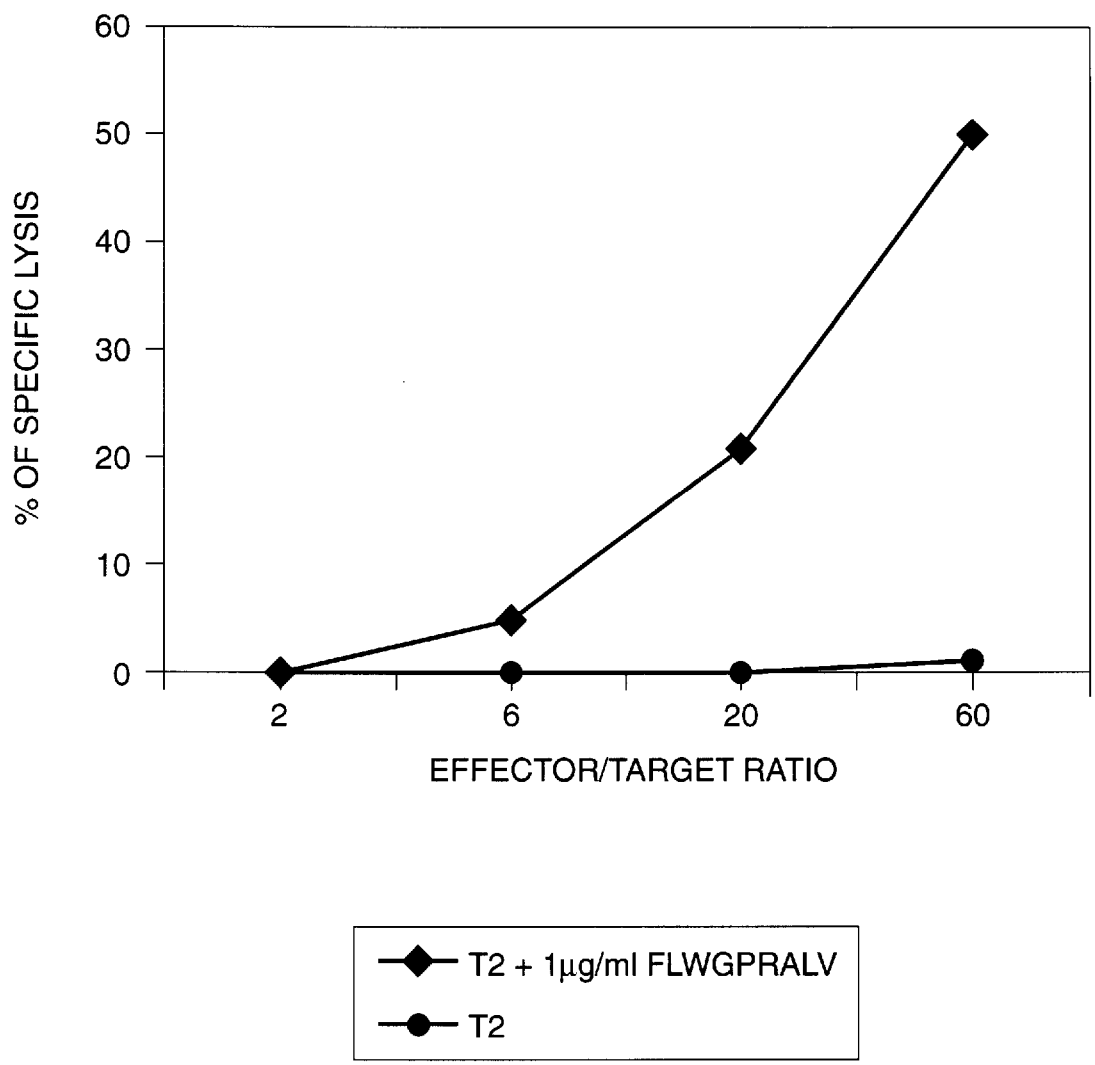
FIG. 3 depicts results obtained in experiments designed to determine whether CTLs specific for complexes of peptide and HLA molecule could be provoked. The X axis shows ratio of effector target cells, while the Y axis shows percent lysis, via chromium release.
Figure 4A:
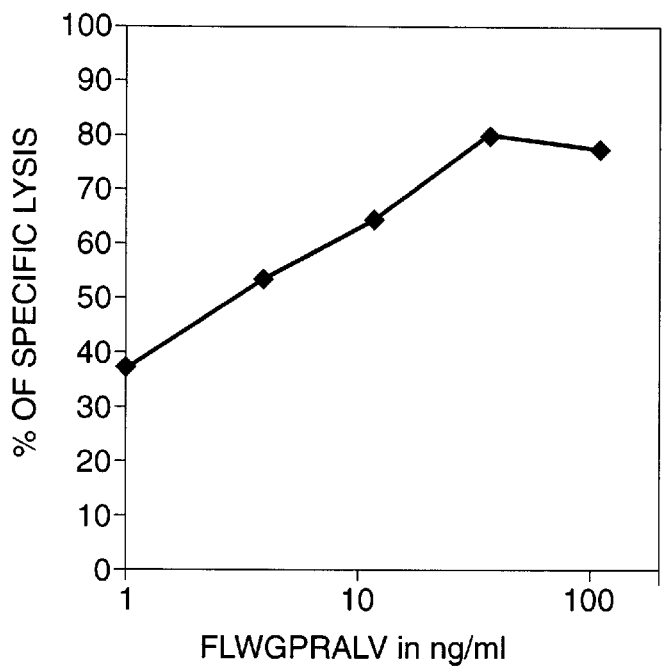
FIGS. 4A, 4B, 4C and 4D show the percentage of lysis obtained with each of four specific CTLs found as a result of limiting dilution assays. The targets were T2 cells.
Figure 4B:
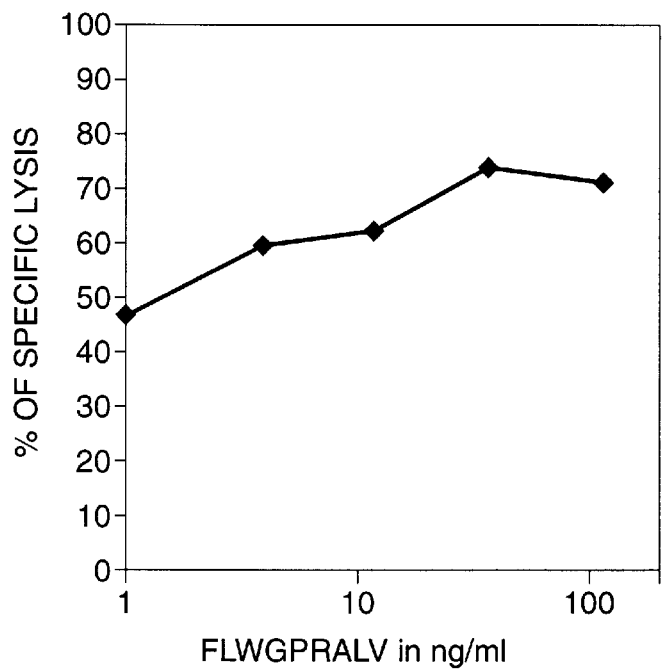
Figure 4C:
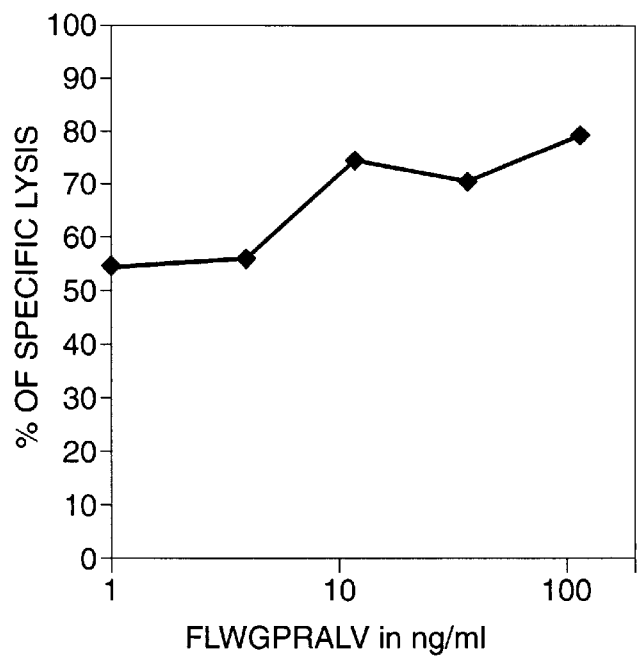
Figure 4D:
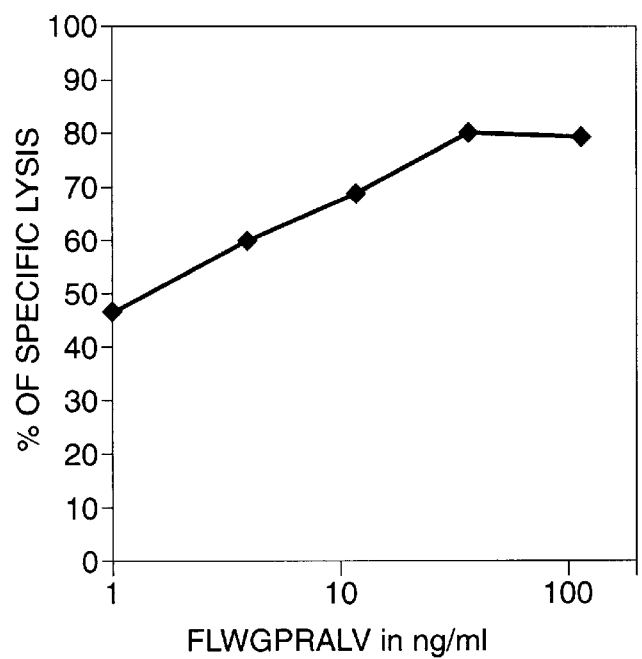
Figure 5A:
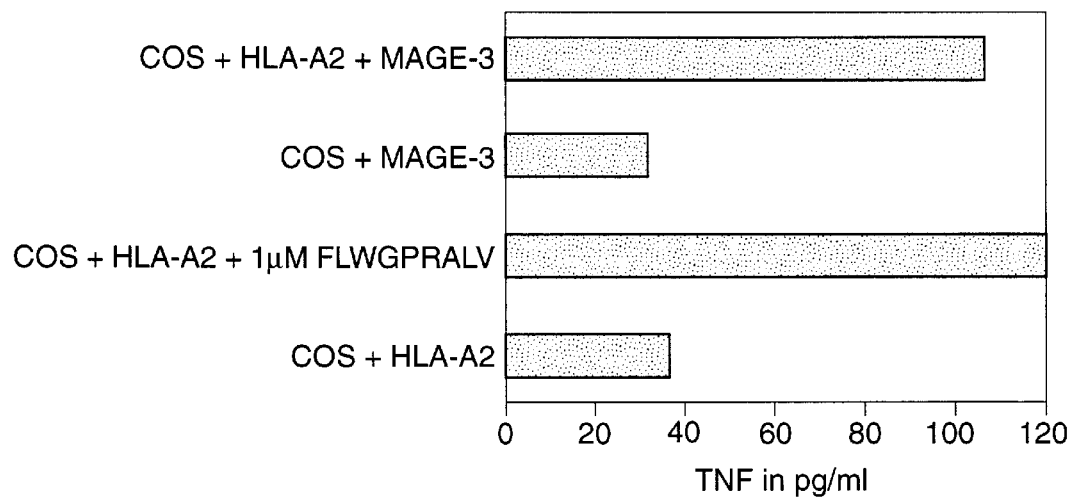
FIGS. 5A–5D show results obtained with each of the CTLs when tested against a variety of transformed and non-transformed cells.
Figure 5B:
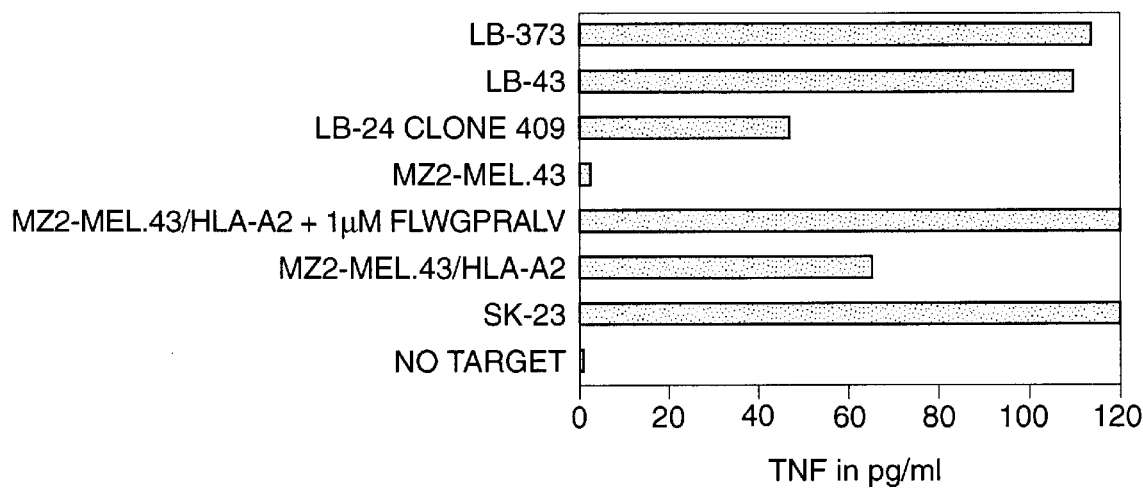
Figure 5C:
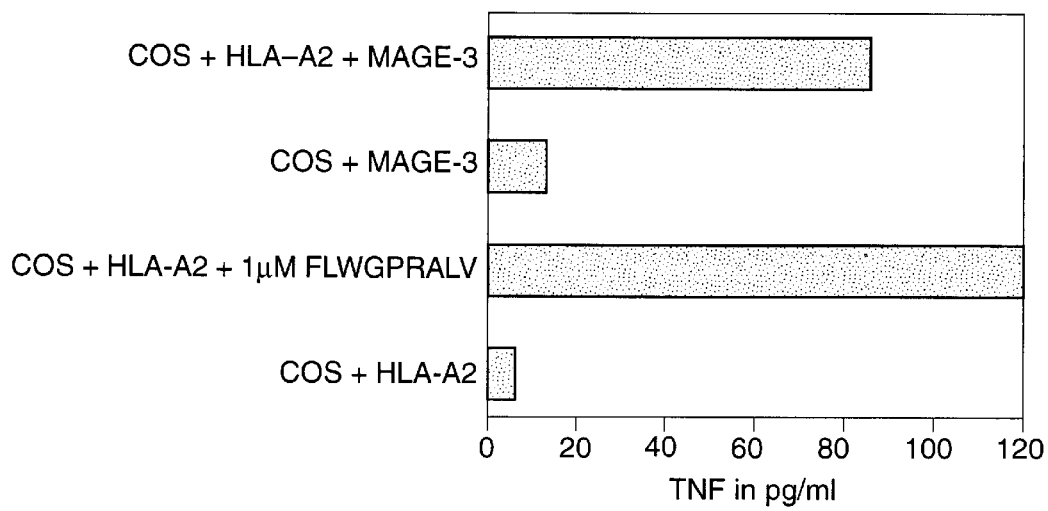
Figure 5D:
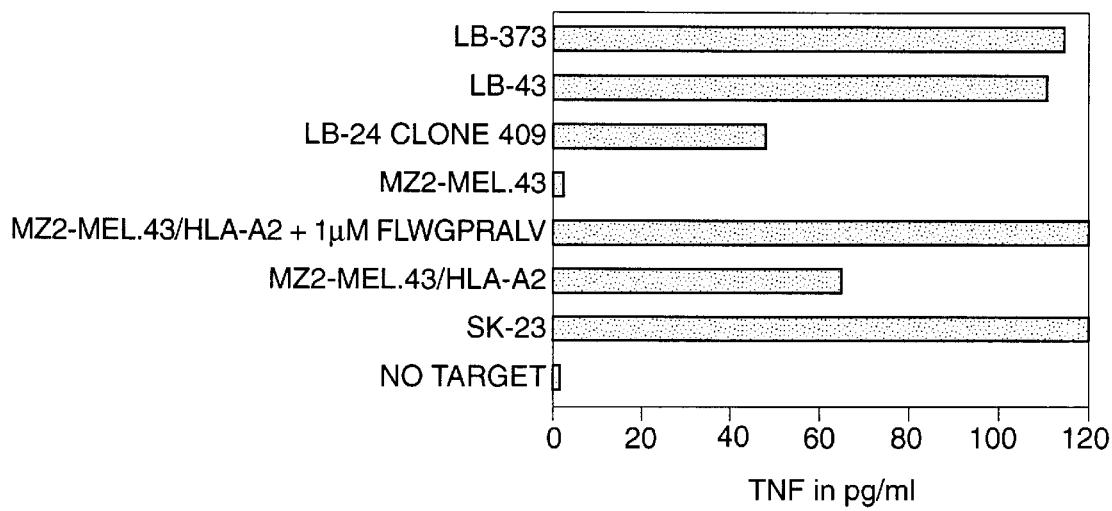
Figure 5E:
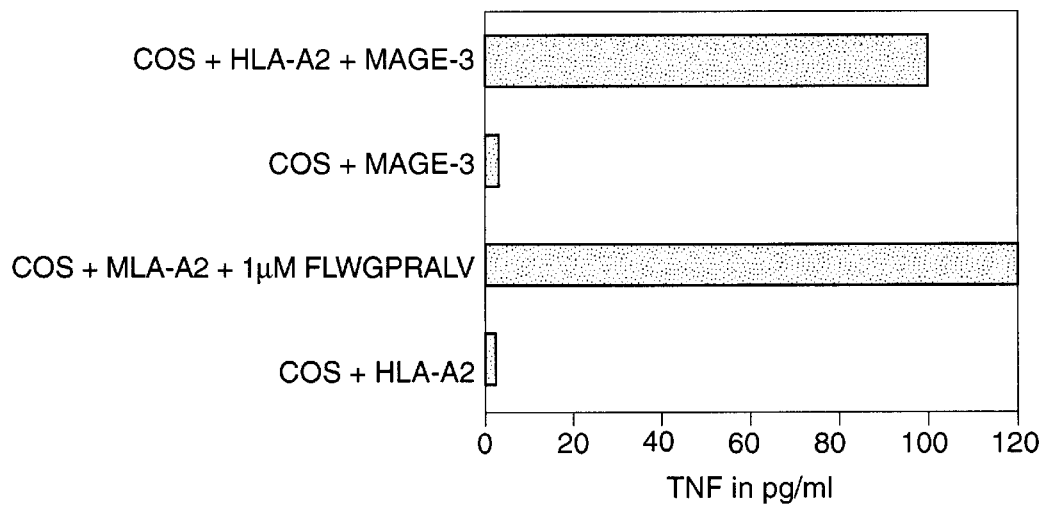
Figure 5F:
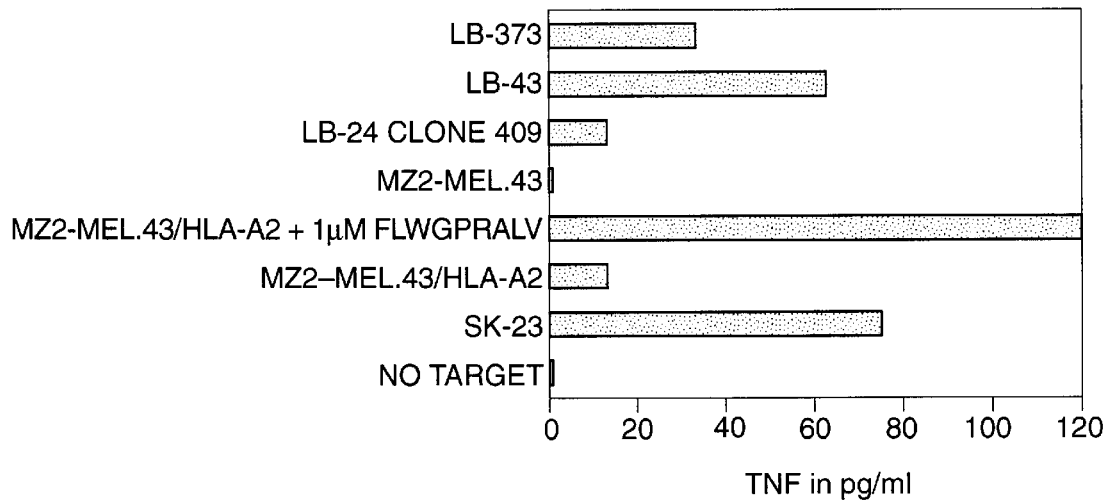
Figure 5G:
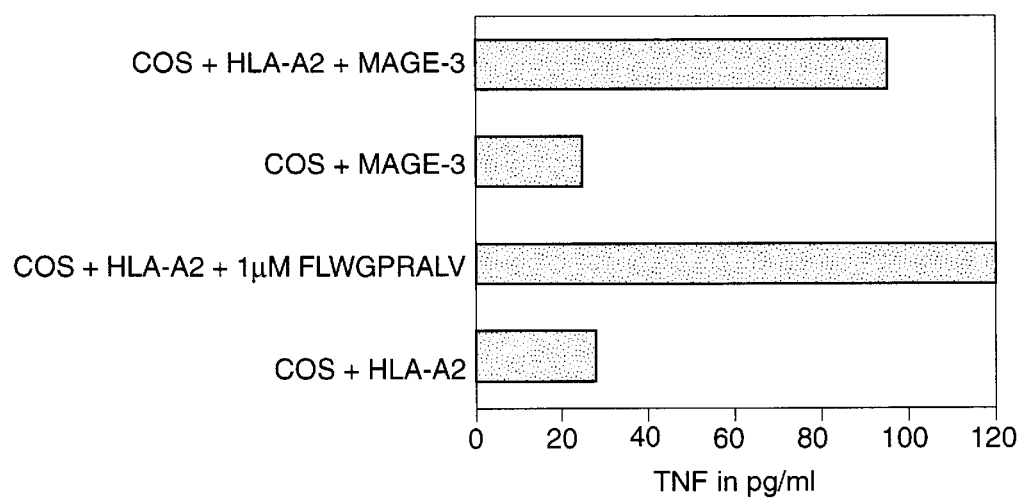
Figure 5H:
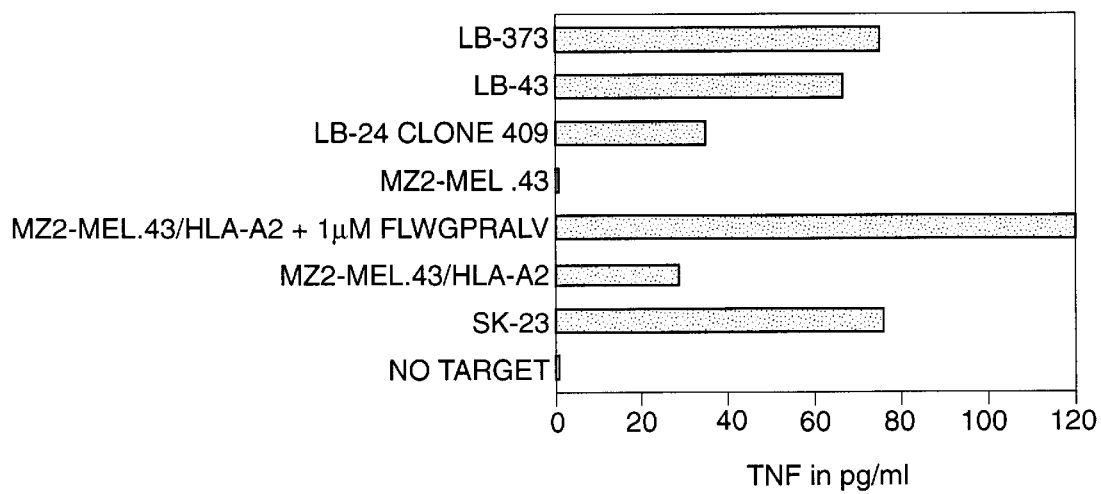

FIG. 3 shows the results. The X-axis shows the ratio of effector/target cells, while the Y axis depicts the percent of specific lysis, determined by measuring chromium release, in accordance with Boon, et al., J. Exp. Med. 152: 1184 (1980), incorporated by reference in its entirety. In each test well, non-specific lysis was eliminated by adding 50,000 K562 cells to the 1,000 $^{51}$Cr labelled T2 target cells employed. The K562 cells act to eliminate non-specific lysis, as Natural Killer, or "NK" cells preferentially lyse this line.

It is clear that the peptide, when presented by HLA-A2, provoked lysis of the T2 cells.

Example 5

The work described in example 4 led to the generation of a mixed culture of CD8+ T cells specific for complexes of SEQ ID NO: 6 and its presenting HLA-A2 molecules, and non-specific CTLs. To isolate CTL clones of the desired specificity, a limiting dilution assay was carried out in accordance with Herin, et al., Int. J. Cancer 39: 390–396 (1987), incorporated by reference, but summarized herein.

On day 29, following Herin, et al., supra, irradiated SK23-MEL cells, known to express MAGE-3 and HLA-A2, were combined with the CTL mixed culture, together with LG2-EBV cells, which acted as feeder cells. Also, 50 U/ml of IL-2, and 5 U/ml IL-4 were added to the mixture. This resulted in the generation of CTL clones 297/19, CTL 297/22, CTL 297/27, and CTL 297/36.

Example 6

In example 4, the induction of lysis of cells presenting the peptide of SEQ ID NO: 6 was shown, using a fixed amount of peptide with varying effector/target ratios. In these experiments, the effector/target ratio was kept constant, and the amount of peptide varied. Again, the $^{51}$Cr release assay of example 4 was used, as were the T2 cells and CTLs of example 4. The four different CTLs of example 5 were used.

FIGS. 4A, 4B, 4C and 4D show these results, and indicate some dose dependency of lysis. When T2 cells were not incubated with peptide, lysis was always below 2%.

Example 7

In another set of experiments, the lytic effect of the peptide of SEQ ID NO: 6 was tested in a model where the host cells did not inherently express HLA-A2.

Samples of cell line COS-7 were used. The cells were transfected with one of (i) genomic DNA for HLA-A2.01 and cDNA for MAGE-3, (ii) genomic DNA for HLA-A2.01 only, or (iii) cDNA for MAGE-3 only. In each case, the transfecting vector was pcDNA/AmpI, where the DNA was ligated to EcoRI adaptors, and cloned into the EcoRI site of the plasmid in accordance with manufacturer's instructions. The recipient cells were seeded, at 15,000 cells/well into tissue culture flat bottom microwells in Dulbecco's modified Eagles Medium ("DMEM") supplemented with 10% fetal calf serum. Cells were incubated overnight, and medium was removed and replaced by 30 ul/well of DMEM containing 10% Nu serum, 400 ug/ml DEAE dextran, 100 μM chloroquine, and 100 ng of the plasmids made as described herein. As a further control, COS-7 cells transfected with HLA-A2 alone (via HLA-A2.01 in pcDNA/AmpI), were preincubated for one hour with 1 μM of the peptide of SEQ ID NO: 6, following example 4, supra.

In addition, melanoma cell lines which were known to express MAGE-3 and which were HLA-A2+ were used. These cell lines are identified in the figures as LB 373, LB43, LB24 clone 409, and SK23. Cell line MZ2-MEL.43 is HLA-A2−. In additional tests the line was also transfected with the HLA-A2 gene in pcDNA/AmpI.

A TNF release assay was used, following Traversari, et al, Immunogenetics 35: 145–152 (1992), incorporated by reference herein, but outlined below, together with the modifications thereto. Specifically, 1500 CTLs were combined with 30,000 target cells (CTLs were one of the clones discussed supra). The cells were cultured together, in the presence of 25 u/ml of IL-2. Twenty-four hours later, supernatants from the cultures were tested against WEHI 164 clone 13 cells, which are sensitive to TNF. Sensitivity was increased by adding LiCl to the WEHI 164 clone 13 cells (20 mM), in accordance with Beyart, at al, PNAS 86: 9494–9498 (1989).

The results of these experiments are depicted in FIGS. 5A–5D. Each figure presents TNF release (pg/ml), for a different CTL clone, for transfectants (top panel, each figure), and tumor cell lines (bottom panel). The figures show that MAGE-3 transfection alone is insufficient to provoke lysis, nor is HLA-A2 transfection. Transfection with both MAGE-3 and HLA-A2 was sufficient, which is not surprising. What is unexpected, however, is the increase in lysis secured when peptide SEQ ID NO: 6 is added to cells transfected with HLA-A2 alone. Note this pattern in the second panel as well, where the data for "MZ2-MEL.43/HLA-A2+1 μM SEQ ID NO: 6" demonstrated superior lysis to all others. These patterns, as indicated, are repeated over all CTL clones tested.

Example 8

An additional set of experiments were carried out to test the lytic affect of the peptide in a chromium release assay on tumor cells. The TNF assay of example 6, supra, is more sensitive than a chromium release assay, so the latter would confirm results of the TNF assay.

The nature of the $^{51}$Cr release assay was described supra, with reference to Boon, et al (1980). Using the same assay, CTL clones 297/19 and 297/22 were used, with a series of target cells known to be HLA-A2 positive. The cell lines LB43 and SK23 are also known to express MAGE-3. Cell line T2 is HLA-A2+, and MAGE-3−.

The table, which follows, sets forth the data obtained at various ratios of effector/target cells. The ratios, however, are all very low. The data are presented as percentage of cell lysis, after four hours, and 20 hours.

TABLE 1 lysis of HLA-A2 + MAGE-3+ cells.
Chromium labelled targets were incubated with CTL 4 hours or 20 hours before collecting supernatants

| effector cells | E/T | Incubation | LB-48 4 h | LB-43 20 h | SK22 4 h | SK23 20 h | T2 4 h | T2 20 h |
|---|---|---|---|---|---|---|---|---|
| PENNA 297/19 | 10 | | 15 | 78 | 6 | 30 | 0 | 8 |
| | 3 | | 14 | 72 | 8 | 50 | 4 | 0 |
| | 1 | | 16 | 64 | 8 | 31 | 1 | 9 |
| | 0, 3 | | 7 | 59 | 3 | 11 | 0 | 8 |
| | 0, 1 | | 3 | 21 | 1 | 7 | 0 | 10 |
| | 0, 03 | | 4 | 26 | 1 | 3 | 1 | 7 |
| PENNA 297/22 | 10 | | 19 | 80 | 10 | 31 | 0 | 1 |
| | 3 | | 15 | 74 | 12 | 40 | 2 | 3 |
| | 1 | | 17 | 82 | 13 | 52 | 3 | 8 |
| | 0, 3 | | 22 | 83 | 3 | 25 | 1 | 17 |
| | 0, 1 | | 8 | 48 | 1 | 11 | 0 | 11 |
| | 0, 03 | | 5 | 11 | 1 | 1 | 1 | 8 |
| | | min | 124 | 487 | 84 | 276 | 54 | 219 |
| | | MAX | 671 | 830 | 734 | 720 | 352 | 338 |
| | | % apontral | 12% | 35% | 8% | 25% | 15% | 39% |

Even at low E/T ratios, there was significant lysis, showing the ability to induce lysis.

Example 9

An experiment along the lines of the work set out in Example 7 was carried out. The stimulation of CTL clones 297/19 and 297/22, by COS-7 cells transfected with pcDNAI/Amp containing the HLA-A2 gene, and one of cDNAs coding for MAGE-12 or MAGE-3 was tested. As controls, cells were transfected with one of HLA-A2, MAGE-3, or MAGE-12 cDNA. To provide a control for expression of HLA-A2, a sample of transfected COS cells was preincubated for one hour with the peptide of SEQ ID NO: 6. A total of 1500 CTLs were added to transfectants, and TNF content of supernatant was estimated, 24 hours later, by assaying for toxicity on WEHI-164 clone 13 cells, in the manner described supra.

Figure 6A:
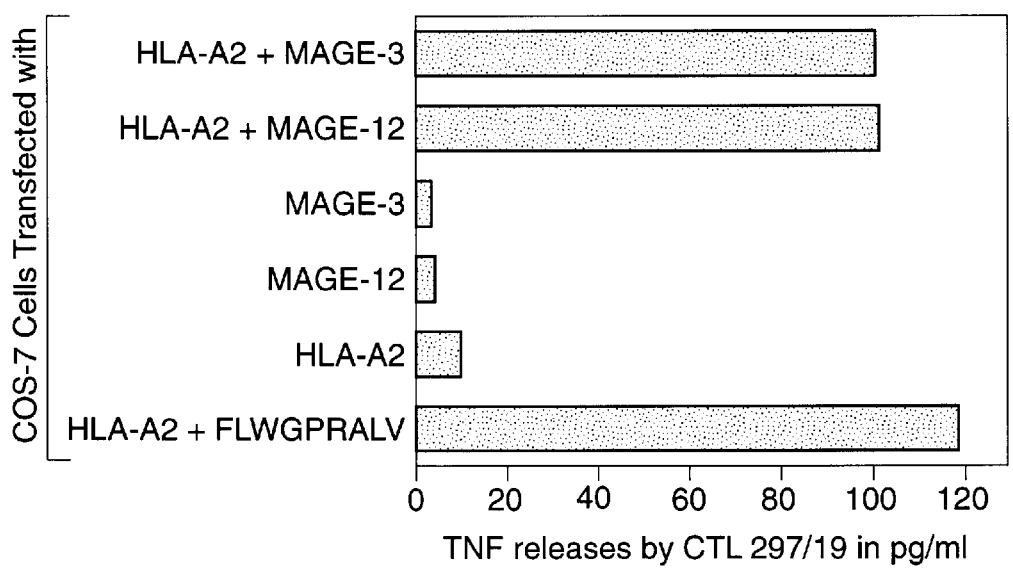
FIGS. 6A and 6B show results obtained when COS-7 cells were transfected by one or more of HLA-A2, MAGE-3, and MAGE-12 cDNA. The assay employed was a TNF release assay, using WEHI-164 clone 13 cells. In control experiments, only one of HLA-A2, MAGE-3, and MAGE-12 cDNA was used.
Figure 6B:
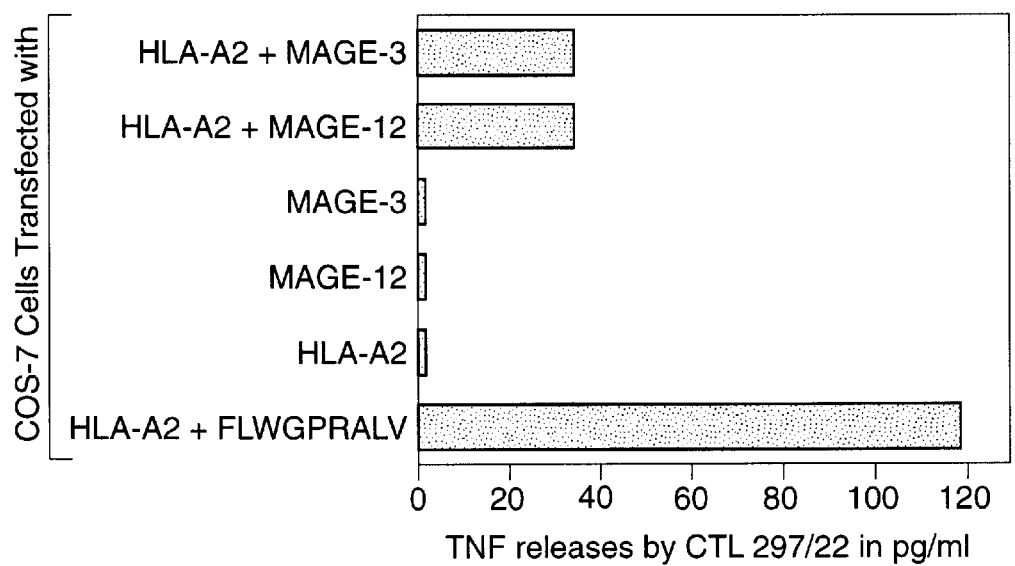

As is shown by FIGS. 6A and 6B, MAGE-3 and MAGE-12 were processed to tumor rejection antigens which appear to be identical. The predicted amino acid sequence for the MAGE-12 tumor rejection antigen precursor contains a stretch of amino acids identical to SEQ ID NO: 6. Thus, it can be said that one of a number of MAGE TRAPs may give rise to the same tumor rejection antigen.

Example 10

In a further set of experiments, the CTL clones 297/19 and 297/22 were tested with melanoma cell lines which had been typed previously, as being HLA-A2+ and MAGE-3+. The experiments utilized 30,000 tumor cells (target cells), and 1500 CTLs (effector cells), combined as a co-culture. TNF release into the coculture was determined via the methodologies discussed supra, using the WEHI-164 clone 13 line.

Figure 7A:
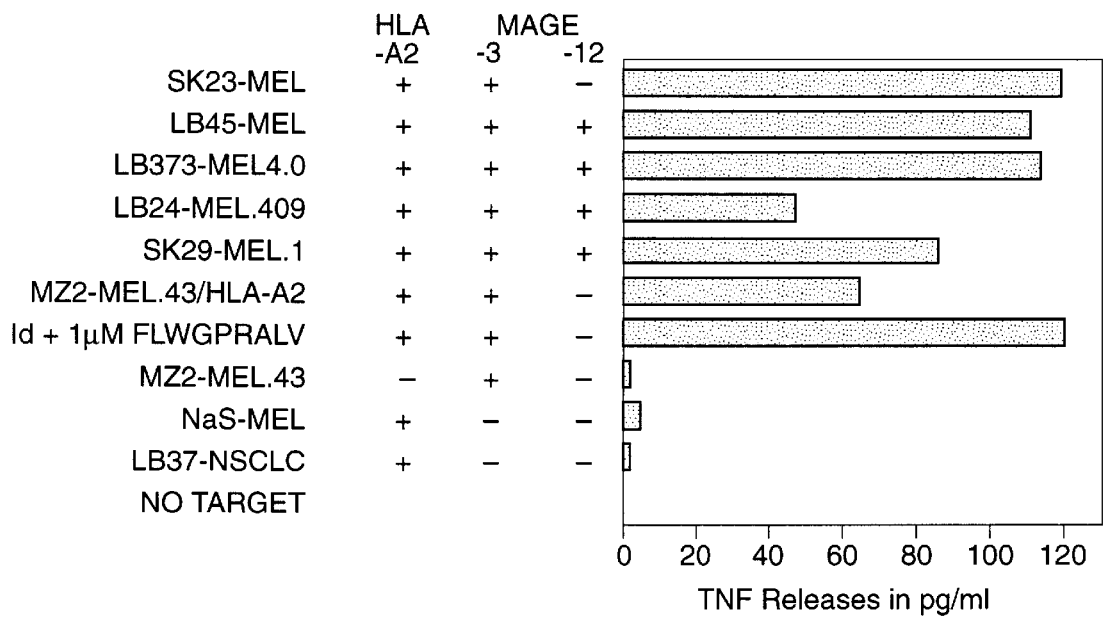
FIGS. 7A and 7B show result in a TNF release assay in which cells which were HLA-A2⁺/MAGE-3⁺ were compared to cells which were positive for MAGE-3 or HLA-A2, but not both.
Figure 7B:
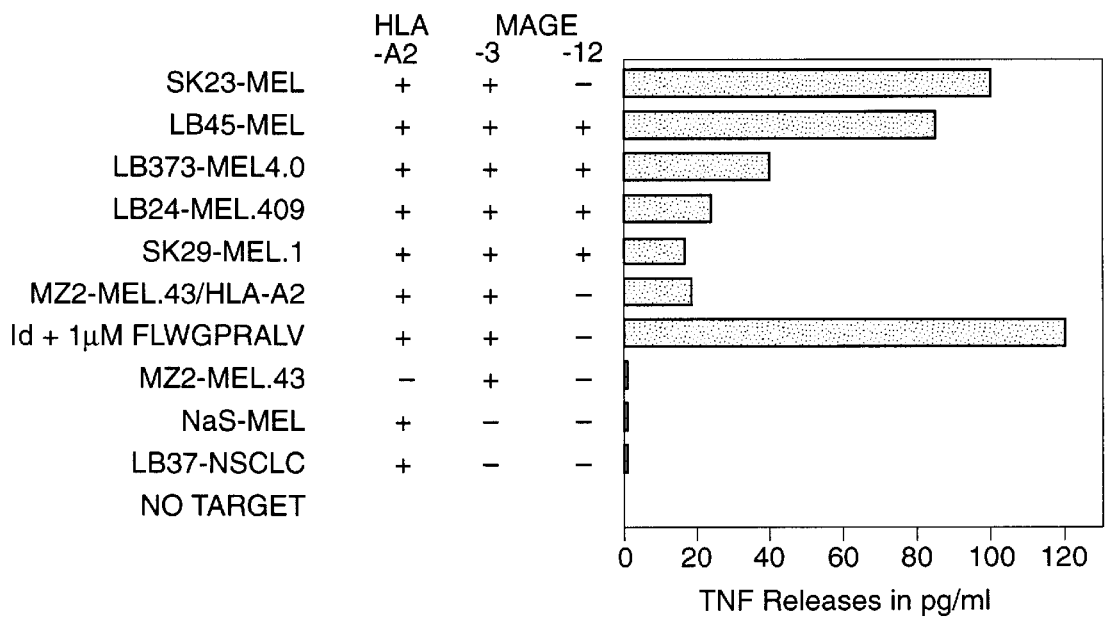

FIGS. 7A and 7B, corresponding to CTL 297/19 and CTL 297/22, respectively, show that the CTLs lysed lines which were HLA-A2+ and MAGE-3+, but not those lines which were positive for one, but not the other. Note that cell line MZ2-MEL.43/HLA-A2 which is HLA-A2+/MAGE-3+ is MZ2-MEL.43, (HLA-A2−, MAGE-3+), which has been transfected with HLA-A2.

Example 11

In a further example the lysis of HLA-A2+/MAGE-3+ melanoma cell lines, by CTL clone 297/22, was tested. In these experiments, the target melanoma cell lines were preincubated with 100 u/ml IFN-γ and 1 ng/ml TNFα for 72 hours, and labelled with $^{51}$Cr, in the same manner described supra. The labelled cells were incubated with effector cells, at various ratios. The $^{51}$Cr release was measured after five hours.

Figure 8:
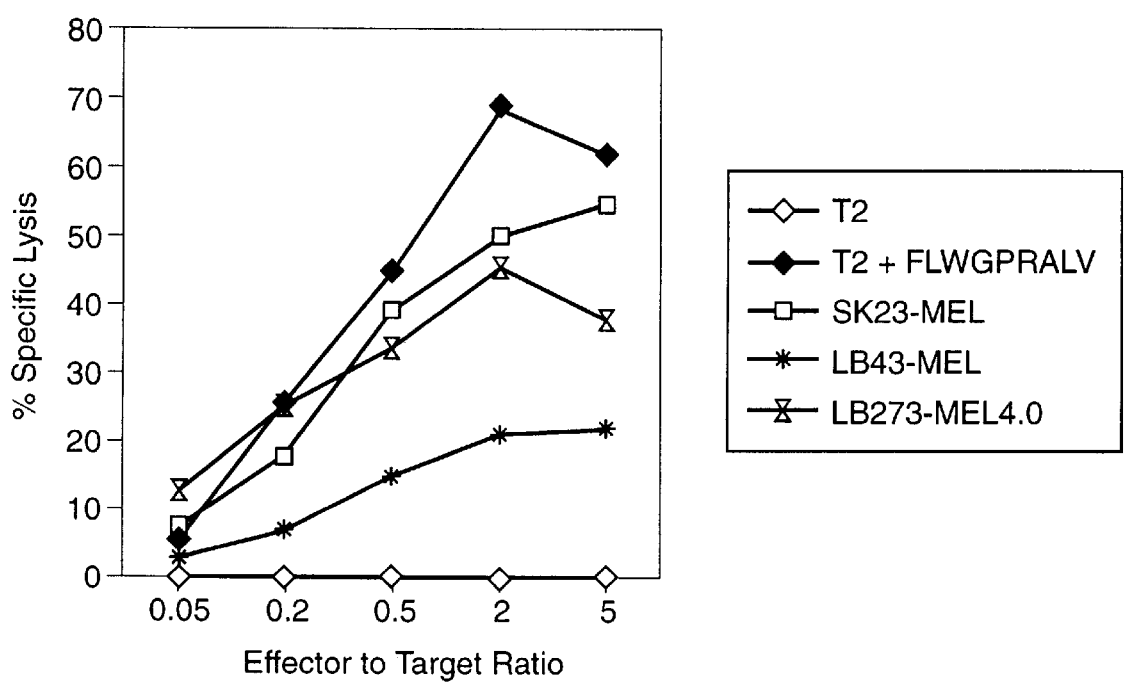
FIG. 8 presents a $^{51}$Cr release assay where HLA-A2⁺ cells were tested in combination with SEQ ID NO: 6 (cell line T2), as were cells which are HLA-A2⁺/MAGE-3⁺ (i.e., SK23-MEL, LB43-MEL, LB273-MEL 4.0).

The results are depicted in FIG. 8, and again show that the tumor cells are presenting complexes of HLA-A2 and the peptide of SEQ ID NO: 6.

The foregoing describes the identification of peptides derived from the MAGE-3 tumor rejection antigen precursor which interact with MHC class I molecule HLA-A2. Of particular interest, and a part of the subject matter of the present invention, are the peptides represented by SEQ ID NOS: 1–10. These peptides are easily synthesized by Merrifield Synthesis or other peptide synthesis methodologies.

Of special interest are peptides which satisfy the following formulas:

and

where n is 4 or 5, and Xaa is any amino acid. Especially preferred are peptides such as SEQ ID NO: 6, which is exemplary of this class.

The peptides, as indicated, complex with HLA-A2 molecules, and these complexes have been immunoprecipitated, thus leading to another feature of the invention, which is isolated complexes of the HLA-A2 molecule and either one of these peptides.

Both the peptides and the complexes are useful in various ways. As was shown, the peptides bind to the HLA-A2 molecule, and thus they are useful in assays to determine whether or not HLA-A2 presenting cells are present in a sample. The peptide is contacted to the sample of interest in some determinable form, such as a labelled peptide (radiolabel, chromophoric label, and so forth), or bound to a solid phase, such as a column or agarose or SEPHAROSE bead, and the binding of cells thereto determined, using standard analytical methods.

Both the peptides and the isolated complexes may be used in the generation of monoclonal antibodies or cytolytic T cell clones specific for the aforementioned complexes. Those skilled in the art are very familiar with the methodologies necessary to accomplish this, and the generation of a cytolytic T cell clone is exemplified supra. As some cancer cells present complexes of MAGE-3 derived peptides such as SEQ ID NOS: 2, 6, 7, 8 and 10 and HLA-A2, these monoclonal antibodies and cytolytic T cells clones serve as reagents which are useful in diagnosing cancer, since no normal, i.e., non-tumorgenic cell have been found which present such complexex. The chromium release assay discussed supra is exemplary of assays which use CTLs to determine targets of interest, and the art is quite familiar with immunoassays and how to carry these out.

Cytolytic T cell clones thus derived are useful in therapeutic milieux such as adoptive transfer. See Greenberg et al., J. Immunol. 136 (5): 1917 (1986); Reddel et al., Science 257: 238 (1992); Lynch et al., Eur. J. Immunol. 21: 1403 (1991); Kast et al., Cell 59: 603 (1989), all of which are incorporated by reference herein. In this methodology, the peptides set forth supra are combined with antigen presenting cells ("APCs") to form stable complexes. Many such methodologies are known, for example, those disclosed in Leuscher et al., Nature 351: 72–74 (1991); Romero et al., J. Exp. Med. 174: 603–612 (1991); Leuscher et al., J. Immunol. 148: 1003–1011 (1992); Romero et al., J. Immunol. 150: 3825–3831 (1993); Romero et al., J. Exp. Med. 177: 1247–1256 (1993), and incorporated by reference herein. Following this, the presenting cells are contacted to a source of cytolytic T cells to generate cytolytic T cell clones specific for the complex of interest. Preferably, this is done via the use of an autologous T cell clone found in, for example, a blood sample, taken from the patient to be treated with the CTLs. Once the CTLs are generated, these are reperfused into the subject to be treated in an amount sufficient to ameliorate the cancerous condition, such as inhibiting their proliferation, etcetera by lysing cancer cells.

Another aspect of the invention, shown in the examples, is the use of the combination of IL-6 and IL-12 to activate T cells, cytolytic T cells in particular. "Activation", as used herein, refers to the ability to cause the T cells to carry out their intended function. In the case of CTLs, of course, this is the recognition and lysis of cells presenting on their surfaces appropriate combinations of peptide and MHC molecule. The activated T cells can then be used diagnostically, e.g., to determine whether a particular peptide/MHC combination is present on a cell subpopulation in a test sample. Also the use of the combined cytokines can facilitate the identification of particular CTLs. It is known that in a CTL sample, only a very small subpopulation is available which is specific to an MHC/peptide combination. By using the cytokines in combination with a sample presenting the desired combination, one can determine activation, via lysis, and compare it to a control value obtained where everything is kept constant except the sample is not mixed with the additional materials. This provides the requisite control value.

Another feature of the invention is a kit useful in the activation of T cells, the kit comprising in separate portions, interleukin-6 and interleukin-12, the two separate portions being contained within a container means. The kits of interest may also include, e.g., a separate portion of peptide to be presented, and/or a vector or coding region for an MHC molecule, or even a vector or coding sequence which codes for both the MHC molecule and the peptide. For example, the peptide may be SEQ ID NO: 6. The vectors may contain an HLA-A2 coding region or a combination of HLA-A2 and SEQ ID NO: 6. Another feature of the invention is a composition consisting essentially of IL-6 and IL-12, in amounts sufficient to activate T cells, such as CTLs.

"IL-6" and "IL-12" as used herein refer to all forms of these molecules, be they naturally occurring or produced recombinantly, human, murine, or any other species, as well as all variations of the molecule which have the same activating properties of IL-6 and IL-12.

The amount of IL-6 and IL-12 used may vary; however, it is preferred to use from about 500 to about 1000 u/ml of IL-6, and from about 1 to about 10 ng/ml of IL-12, although these ranges may vary, in accordance with the artisan's findings.

Other aspects of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Method for activating cytolytic T cells, comprising contacting said cytolytic T cells with a combination of IL-6 and IL-12 and a tumor rejection antigen, the amino acid sequence of which is set forth at SEQ ID NO: 6 in an amount sufficient to activate said cytolytic T cells.

2. The method of claim 1, wherein said IL-6 is administered in an amount of from about 500—about 1000 u/ml, and said IL-12 is administered in an amount of from about 1 to about 10 ng/ml.

3. Non-covalently associated composition of matter consisting essentially of IL-6, IL-12 and a tumor rejection antigen, the amino acid sequence of which is set forth at SEQ ID NO: 6, in an amount sufficient to stimulate cytolytic T cells.

4. The composition of claim 3, wherein said IL-6 is present in an amount ranging from about 500 ug/ml to about 1000 ug/ml.

5. The composition of matter of claim 3, wherein said IL-12 is present in an amount ranging from about 1 ng/ml to about 10 ng/ml.

6. Kit useful in activating cytolytic T cells, comprising a separate portion of each of (i) IL-6, (ii) IL-12, and (iii) a tumor rejection antigen, the amino acid sequence of which is set forth at SEQ ID NO: 6, or a DNA molecule which encodes said tumor rejection antigen, and a container means for holding separate the portions of (i), (ii) and (iii).

7. The kit of claim 6, further comprising a DNA molecule which codes for an HLA-A2 molecule.

* * * * *